US 7,696,167 B2

(12) United States Patent
Kobayashi et al.

(10) Patent No.: US 7,696,167 B2
(45) Date of Patent: Apr. 13, 2010

(54) CYCLIC PEPTIDE COMPOUND

(75) Inventors: Motoo Kobayashi, Tokyo (JP); Satoshi Sasamura, Tokyo (JP); Hideyuki Muramatsu, Tokyo (JP); Yasuhisa Tsurumi, Tokyo (JP); Shigehiro Takase, Tokyo (JP); Kazuki Okada, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 469 days.

(21) Appl. No.: 11/719,921

(22) PCT Filed: Nov. 21, 2005

(86) PCT No.: PCT/JP2005/021742

§ 371 (c)(1),
(2), (4) Date: May 22, 2007

(87) PCT Pub. No.: WO2006/054801

PCT Pub. Date: May 26, 2006

(65) Prior Publication Data

US 2008/0214447 A1    Sep. 4, 2008

(30) Foreign Application Priority Data

Nov. 22, 2004    (AU) .............................. 2004906673

(51) Int. Cl.
*A61K 38/00* (2006.01)
*C12P 21/06* (2006.01)
*A61K 38/12* (2006.01)

(52) U.S. Cl. ..................... 514/11; 435/68.1; 530/317
(58) Field of Classification Search .................. None
See application file for complete search history.

(56) References Cited

U.S. PATENT DOCUMENTS 5,116,816 A * 5/1992 Dreyfuss et al. .............. 514/11

FOREIGN PATENT DOCUMENTS

| EP | 0577544 A1 | * | 2/1993 |
| JP | 05-271267 A | * | 10/1993 |
| WO | WO 02/32447 A2 | | 4/2002 |
| WO | WO 2005/021028 A1 | | 3/2005 |
| WO | WO 2005/032576 A1 | | 4/2005 |
| WO | WO 2006/038088 A1 | | 4/2006 |
| WO | WO 2006/039668 A2 | | 4/2006 |

OTHER PUBLICATIONS

Translation to English for JP 05-271267A. FR901459, Its Manufacturing Method and Applications. Date Oct. 1993, 30 pages.*
Koichi Watashi, et al., "Cyclosporin A Suppresses Replication of Hepatitis C Virus Genome in Cultered Hepatocytes", Hepatology, XP009047548, vol. 38, No. 5, Nov. 2003, pp. 1282-1288.
Mina Nakagawa, et al., "Specific inhibition of hepatitis C virus replication by cyclosporin A" Biochemical and Biophysical Research, XP004479114, vol. 313, No. 1, Jan. 2, 2004, pp. 42-47.
Kazutoshi Sakamoto, et al., "FR901459 A Novel Immunosuppressant Isolated from *Stachybotrys chartarum* No. 19392. Taxonomy of the Producing Organism, Fermentation, Isolation, Physico-Chemical Properties and Biological Activities", Journal of Antibiotics, XP001109704, vol. 46, No. 12, Dec. 1993, pp. 1788-1798.
A. F. Yassin, et al., "Lentzea gen. nov., a new genus of the order Actinomycetales", International Journal of Systemic Bacteriology, XP002356553, vol. 45, No. 2, 1995, 1 page.

* cited by examiner

*Primary Examiner*—Cecilia Tsang
*Assistant Examiner*—Marcela M Cordero Garcia
(74) *Attorney, Agent, or Firm*—Oblon, Spivak, McClelland, Maier & Neustadt, L.L.P.

(57)    ABSTRACT

A cyclic peptide compound of the following general formula (I): Wherein $R^1$, $R^2$ and $R^3$ are defined in the description, or a salt thereof. The compound (I) is useful for the prophylactic and/or therapeutic treatment of hepatitis C.

9 Claims, No Drawings

CYCLIC PEPTIDE COMPOUND

CROSS-REFERENCE TO RELATED APPLICATIONS

The present application is a 35 U.S.C. §371 National Stage patent application of International patent application PCT/JP05/021742, filed on Nov. 21, 2005, which claims priority to Australian patent application AU 2004-906673, filed on Nov. 22, 2004.

TECHNICAL FIELD

The present invention relates to a new compound. More particularly, the present invention relates to a new cyclic peptide compound or a salt thereof having inhibitory activity against the RNA replication of hepatitis C virus (hereafter referred to as HCV) replicon. In particular, the present invention relates to a new peptide compound or a salt thereof, to a process for preparation thereof, to a pharmaceutical composition comprising the new cyclic peptide compound or a salt thereof, and to a method for the prophylactic and/or therapeutic treatment of hepatitis C in a human being or animal.

BACKGROUND ART

The estimated number of HCV carriers is about 170 million worldwide (about 3%) and about 1.5 million in Japan. Even in the combination therapy of using interferon (hereafter referred to as IFN) and ribavirin (Virazole), available as a first option for treatment, its effectiveness is 40% for all types of HCV. Furthermore, its effectiveness is only 15 to 20% for IFN-resistant virus (genotype 1b), particularly abundantly found in Japan. On the other hand, the combination therapy has side effects frequently. It is thus difficult to get rid of the virus completely by using currently available treatment methods. In the case when chronic hepatitis cannot be cured completely, the hepatitis will securely develop into cirrhosis hepatitis (30%) or hepatocellular carcinoma (25%). In Europe and the United States, hepatitis C has been a major indication for liver transplant. However, the redevelopment of HCV occurs frequently even in transplanted livers. For these reasons, the needs for new agents being improved in both effectiveness and safety, having higher antiviral effects and capable of inhibiting hepatitis C are very strong in society.

DISCLOSURE OF THE INVENTION

The object cyclic peptide compound in the present invention is a new compound, and can be represented by the following general formula (I):

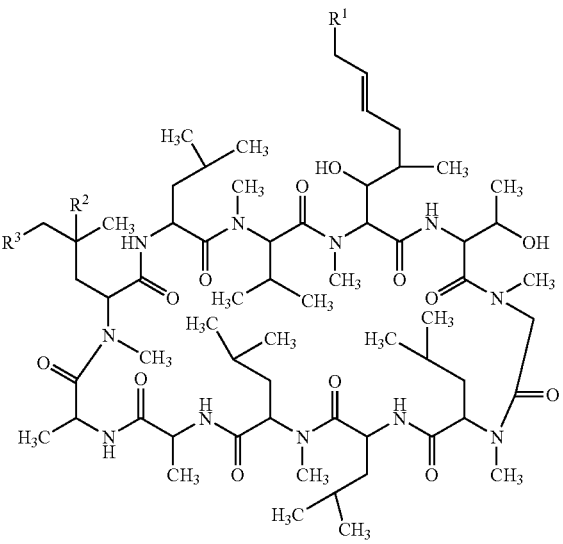

(I)

wherein
$R^1$ is hydrogen or hydroxy,
$R^2$ is hydrogen or hydroxy, and
$R^3$ is hydrogen or hydroxy,
Providing that when $R^1$ is hydrogen,
then at least one of $R^2$ and $R^3$ is hydroxy,
or a salt thereof.

The compound (I) or a salt thereof in the present invention can be prepared by the processes as illustrated in the following reaction schemes.

Process 1

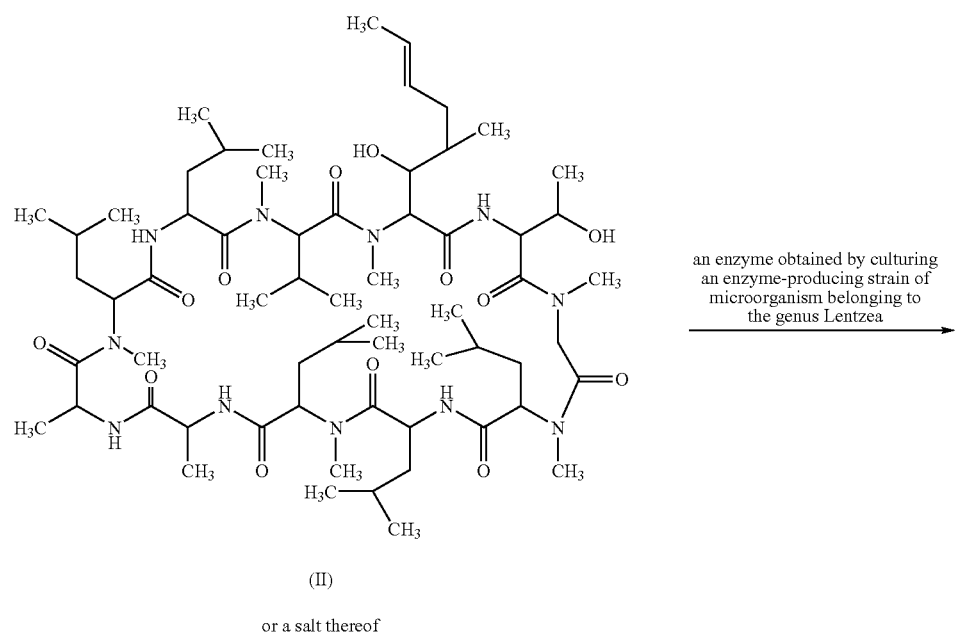

(II)

or a salt thereof

-continued

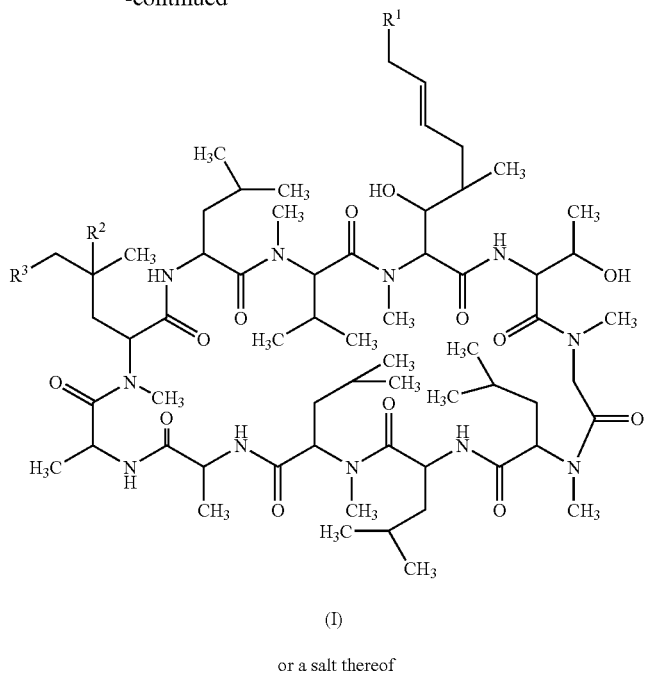

(I)

or a salt thereof wherein $R^1$, $R^2$ and $R^3$ are as defined above.

Suitable salts of the object compound (I) are conventional pharmaceutically acceptable and non-toxic salts, and may be a salt with a base or an acid addition salt, for example, a salt with an inorganic base (such as an alkali metal salt, e.g. sodium salt, potassium salt, etc., an alkaline earth metal salt, e.g. calcium salt, magnesium salt, etc., an ammonium salt), a salt with an organic base (such as an organic amine salt, e.g. triethylamine salt, diisopropylethylamine salt, pyridine salt, picoline salt, ethanolamine salt, triethanolamine salt, dicyclohexylamine salt, N'N'-dibenzylethylenediamine salt, etc.), an inorganic acid addition salt (such as hydrochloride, hydrobromide, sulfate, phosphate, etc.), an organic carboxylic acid or sulfonic acid addition salt (such as formate, acetate, trifluoroacetate, maleate, tartrate, gluconate, fumarate, methanesulfonate, benzenesulfonate, toluenesulfonate, etc.), a salt with a basic or acidic amino acid (such as arginine, aspartic acid, glutamic acid, etc.) and the like.

The compound (II) or a salt thereof can be produced by fermentation of fungus (*Stachybotrys chartarum* No. 19392: deposit number FERM BP-3364) according to the method described in Japanese Laid-open Patent Application Hei 5-271267, for example.

The process for preparing the object compound (I) or a salt thereof of the present invention is explained in detail below.

Process 1

The object compound (I) or a salt thereof can be prepared by contacting a compound (II) or a salt thereof with an enzyme, which can be obtained by fermentation of an enzyme-producing strain of microorganism belonging to the genus *Lentzea*.

The fermentation process is explained in detail below.

(1) Microorganism:

The enzyme can be obtained by fermentation of an enzyme-producing strain of microorganism belonging to the genus *Lentzea* such as *Lentzea* sp. No. 7887 in a nutrient medium.

Strain No. 7887 was isolated from a soil sample collected at Ibaraki Prefecture, Japan. For the taxonomic study of strain No. 7887, the methods and media described by Hamada[1] were employed.

The observations were made after 14 days cultivation at 30° C. The morphological observations were made on the cultures grown on ⅕ yeast extract-starch agar containing 0.4 g of yeast extract (Daigo Eiyo, Osaka, Japan), 2 g of soluble starch, and 16 g of agar in 1000 ml of tap water (adjusted to pH 7.2 with 1N NaOH before sterilized), by using an optical microscope and a scanning electron microscope. Carbon utilization was determined on Pridoham and Gottlieb's medium[2]. The color names used in this study were taken from Methuen Handbook of Colour[3]. The chemotaxonomic characterization was performed by procedure of Suzuki et al[4]. The phylogenetic analysis of the 16S rDNA sequence was performed by the method of Nakagawa et al.[5]. The 16S rDNA sequences of type strains were obtained from DDBJ data base[6]. The phylogenetic tree was constructed by the neighbor-joining methods[7] in CLUSTAL X package (version 1.8)[8].

(2) Morphological Characteristics:

The substrate mycelium was developed well and branched irregularly and penetrated the agar, forming compact colonies on the agar surface. The aerial mycelium was moderately developed on ⅕ yeast extract-starch agar, glycerol-asparagine agar, tyrosine agar, Czapek agar, yeast-starch agar and glucose-asparagine agar, and fragmented into rod-shaped elements. Sclerotic granules, sporangia and motile spores or fragments were not observed.

(3) Cultural and Physiological Characteristics:

The results of cultural and physiological characteristics are shown in Table 1 and 2 respectively. Reverse side color of growth were reddish brown, orange red, brownish red, brownish orange, light orange, orange, and pale orange. Melanoid pigments were not produced in trypton-yeast extract broth and pepton-yeast extract-iron agar. Soluble pigments were produced in yeast extract-malt extract agar, oatmeal agar, and inorganic salts-starch agar, glycerol-asparagine agar, Tyrosine agar, Bennett's agar, Czapek agar, yeast-starch agar, glucose-asparagine agar, sucrose-nitrate agar. Mycerial mass color and soluble pigments were not pH sensitive. L-Arabinose, D-xylose, D-glucose, D-fructose, sucrose, inositol, D-mannitol, cellobiose, dextrin, D-galactose, glycerol, D-mannose, Maltose, D-melibiose, soluble starch, and trehalose were utilized as carbon sources but L-rhamnose, raffinose, adonitol, dextran, dulcitol, inulin, lactose, D-melezitose, sorbitol, L-sorbose, and xylitol were not utilized.

Strain No. 7887 was able to grow in the temperature range of from 10.5 to 32.5° C., with the growth optimum at 31.0° C.

(4) Chemotaxonomical Characteristics:

The cell wall contained meso-diaminopimelic acid and no characteristic sugars (wall chemotype III).

(5) Analysis of 16S rDNA Sequences:

The partial sequence of strain No. 7887 is shown in Table 3. Similarity values of the 16S rDNA between strain No. 7887 and members of the genus *Lentzea* are 97.2-99.1%, and they make single cluster on the phylogenetic tree.

(6) Classification:

Based on the morphological and chemical characteristics and phylogenetic analysis described above, strain No. 7887 is considered to belong to the genus *Lentzea*[9,10,11]. Therefore, this strain was designated as *Lentzea* sp. No. 7887.

A culture of *Lentzea* sp. No. 7887 thus named has been deposited at the International Patent Organism Depositary (IPOD) National Institute of Advanced Industrial Science and Technology, AIST Tsukuba Central 6, 1-1, Higashi 1-chome, Tsukuba-shi, IBARAKI, 305-8566, JAPAN, on Aug. 3, 2004 under the number of FERM BP-10079.

TABLE 1

Cultural characteristics of strain No. 7887

| Medium | Cultural characteristics |
|---|---|
| Yeast extract-malt extract agar (ISP-2) | G: Good<br>A: Thin, white<br>R: Reddish brown (8E8)<br>S: Brown |
| Oatmeal agar (ISP-3) | G: Moderate<br>A: Thin, white<br>R: Orange red (8A8)<br>S: Orange |
| Inorganic salts-starch agar (ISP-4) | G: Good<br>A: Scant, white<br>R: Brownish red (9C7)<br>S: Light brown |
| Glycerol-asparagine agar (ISP-5) | G: Good<br>A: Moderate, white<br>R: Brownish orange (7C7)<br>S: Brown |
| Peptone-yeast extract-iron agar (ISP-6) | G: Moderate<br>A: Scant, white<br>R: Light orange (5A5)<br>S: Not detected |
| Tyrosine agar (ISP-7) | G: Good<br>A: Moderate, white<br>R: Brownish orange (7C7)<br>S: Brown |

TABLE 1-continued

Cultural characteristics of strain No. 7887

| Medium | Cultural characteristics |
|---|---|
| Bennett's agar | G: Good<br>A: Thin, white<br>R: Orange red (8B8)<br>S: Brown |
| Czapek agar | G: Moderate<br>A: Moderate, white<br>R: Orange (6A6)<br>S: Light orange |
| Yeast-starch agar | G: Moderate<br>A: Moderate, white<br>R: Orange red (8B8)<br>S: Light brown |
| Glucose-asparagine agar | G: Moderate<br>A: Moderate, yellowish white (4A2)<br>R: Pale orange (5A3)<br>S: Light brown |
| Sucrose-nitrate agar | G: Moderate<br>A: Thin, yellowish white (4A2)<br>R: Orange (5A6)<br>S: Light brown |
| Nutrient agar | G: moderate<br>A: Thin, white<br>R: Light orange (5A5)<br>S: Not detected |

Abbreviation:
G: growth,
A: aerial mycelium,
R: reverse side color,
S: soluble pigment

TABLE 2

Physiological characteristics of strain No. 7887

| Conditions | Characteristics |
|---|---|
| Temperature range for growth (° C.) | 10.5-35.2 |
| Optimum temperature for growth (° C.) | 31.0 |
| Production of Melanoid pigments | − |
| Production of soluble pigments | + |
| Hydrolysis of gelatin | + |
| Carbon utilization | |
| L-Arabinose | + |
| D-Xylose | + |
| D-Glucose | + |
| D-Fructose | + |
| Sucrose | + |
| L-Rhamnose | − |
| Raffinose | − |
| Inositol | + |
| D-Mannitol | + |
| Adonitol | − |
| Cellobiose | + |
| Dextran | − |
| Dextrin | + |
| Dulcitol | − |
| D-Galactose | + |
| Glycerol | + |
| Inulin | − |
| Lactose | − |
| D-Mannose | + |
| Maltose | + |
| D-Melezitose | − |
| D-Melibiose | + |
| Sorbitol | − |
| Soluble starch | + |
| L-Sorbose | − |
| Trehalose | + |
| Xylitol | − |
| Sodium acetate (0.1% v/v) | ± |

TABLE 2-continued

Physiological characteristics of strain No. 7887

| Conditions | Characteristics |
|---|---|
| tri-Sodium Citrate (0.1% v/v) | ± |
| Malonic acid disodium salt (0.1% v/v) | ± |
| Propionic acid sodium salt (0.1% v/v) | ± |
| Pyruvic acid sodium salt (0.1% v/v) | ± |

+: positive,
±: weakly positive,
−: negative

Table 3 The partial 16S rDNA sequence of stain No. 7887

```
CGAACGCTGGCGGCGTGCTTAACACATGCAAGTCGAGCGGTAAGGCCCTTCGGGGTACACG    (SEQ ID NO. 1)
AGCGGCGAACGGGTGAGTAACACGTGGGTAACCTGCCCTGTACTCTGGGATAAGCCTTGGA
AACGAGGTCTAATACCGGATACGACCATTGATCGCATGATCGGTGGTGGAAAGTTCCGGCG
GTATGGGATGGACCCGCGGCCTATCAGCTTGTTGGTGGGGTAATGGCCTACCAAGGCGACG
ACGGGTAGCCGGCCTGAGAGGGTGACCGGCCACACTGGGACTGAGACACGGCCCAGACTCC
TACGGGAGGCAGCAGTGGGGAATATTGCACAATGGGCGAAAGCCTGATGCAGCGACGCCGC
GTGAGGGATGACGGCCTTCGGGTTGTAAACCTCTTTCAGCAGGGACGAAGCGCAAGTGACG
GTACCTGCAGAAGAAGCACCGGCTAACTACGTGCCAGCAGCCGCGGTAATACGTAGGGTGC
GAGCGTTGTCCGGAATTATTGGGCGTAAAGAGCTCGTAGGCGGTTTGTCGCGTCGGCCGTG
AAAACTTGGGGCTTAACTCCAAGCTTGCGGTCGATACGGGCAGACTTGAGTTCGGCAGGGG
AGACTGGAATTCCTGGTGTAGCGGTGAAATGCGCAGATATCAGGAGGAACACCGGTGGCGA
AGGCGGGTCTCTGGGCCGATACTGACGCTGAGGAGCGAAAGCGTGGGGAGCGAACAGGATT
AGATACCCTGGTAGTCCACGCCGTAAACGGTGGGTGCTAGGTGTGGGGGGCTTCCACGCCC
TCTGTGCCGCAGCTAACGCATTAAGCACCCCGCCTGGGGAGTACGGCCGCAAGGCTAAAAC
TCAAAGGAATTGACGGGGGCCCGCACAAGCGGCGGAGCATGTGGATTAATTCGATGCAACG
CGAAGAACCTTACCTGGGCTTGACATGGACTAGAAAGCTCTAGAGATAGAGCCTCCCTTGT
GGCTGGTTCACAGGTGGTGCATGGCTGTCGTCAGCTCGTGTCGTGAGATGTTGGGTTAAGT
CCCGCAACGAGCGCAACCCTCGTTCCATGTTGCCAGCACGTAATGGTGGGGACTCATGGGA
GACTGCCGGGGTCAACTCGGAGGAAGGTGGGGATGACGTCAAGTCATCATGCCCCTTATGT
CCAGGGCTTCACACATGCTACAATGGCCGGTACAAAGGGCTGCTAAGCCGTGAGGTGGAGC
GAATCCCATAAAGCCGGTCTCAGTTCGGATCGGGGTCTGCAACTCGACCCCGTGAAGTCGG
AGTCGCTAGTAATCGCAGATCAGCAACGCTGCGGTGAATACGTTCCCGGGCCTTGTACACA
CCGCCCGTCACGTCACGAAAGTCGGTAACACCCGAAGCCCGTGGCTCAACCCGCAAGGGGG
AGAGCGGTCGAAGGTGGGACTGGCGATTGGGACGAAGTCGTAACAAGGTAGCCGTACCGGA
A
```

1) Hamada, M (2001): Identification Manual of Actinomycetes. pp. 37-47. Edited by The Society for Actinomycetes Japan. Tokyo: Business Center for Academic Societies Japan. (in Japanese)
2) Pridoham, T. G. and D. Gottlieb (1948): The utilization of carbon compounds by some Actinomycetales as an acid for species determination: J. Bacteriol. 56: 107-114.
3) Kornerup, A. and J. H. Wanscher (1978): Methuen Handbook of Colour, Methuen, London
4) Suzuki, K & T. Kudo (2001): Identification Manual of Actinomycetes. pp. 49-82. Edited by The Society for Actinomycetes Japan. Tokyo: Business Center for Academic Societies Japan. (in Japanese)
5) Nakagawa, Y., T. Tamura and H. Kawasaki (2001): Identification Manual of Actinomycetes. pp. 83-117. Edited by The Society for Actinomycetes Japan. Tokyo: Business Center for Academic Societies Japan. (in Japanese)
6) DNA Data Bank of Japan: http://www.ddbj.nig.ac.jp/
7) Saitou, N. & M. Nei: The neighbor-joining method: a new method of constructing phylogenetic tree. Mol. Biol. Evol. 6: 514-525, 1987
8) Thompson, J. D.; T. J. Gibson, F. Plewniak, F. Jeanmougin & D. G. Higgins (1997): The Clustal X windows interface: flexible strategies for multiple sequence alignment aided by quality analysis tools. Nucleic Acids Research 24: 4876-4882
9) Yassin, A. F., F. A. Rainey, H. Brzezinka, K. D. Jahnke, H. Weissbrodt, H. Budzikiewicz, E. Stackebrandt, and K. P. Schaal (1995): Lentzea gen. nov., a new genus of the order Actinomycetales.: Int J Syst Bacteriol 45, 357-363.

10) Labeda, D. P., K. Hatano, R. M. Kroppenstedt, and T. Tamura (2001): Revival of the genus Lentzea and proposal for Lechevalieria gen. nov. Int J Syst Evol Microbiol. 51, 1045-1050.

11) Xie, Q., Y. Wang, Y. Huang, Y. Wu, F Ba and Z Liu (2002): Description of *Lentzea flaviverrucosa* sp. nov. and transfer of the type strain of *Saccharothrix aerocolonigenes* subsp. *staurosporea* to Lentzea albida.:Int J Syst Bacteriol 50, 1315-1323

(7) The Preparation of the Object Compound (I) or a Salt Thereof by Contacting a Compound (II) or a Salt Thereof with an Enzyme:

The object compound (I) or a salt thereof can be obtained by contacting the compound (II) or a salt thereof in an aqueous solvent with a crude or purified enzyme solution.

Suitable example of the enzyme may include the one produced by certain microorganisms of the Lentzea or the like, such as Lentzea sp. No. 7887 (FERM BP-10079).

This reaction is usually carried out in an aqueous solution with one or more solvent(s) such as methanol or any other solvent which does not adversely influence the reaction.

The reaction temperature is not critical and the reaction can be carried out at room temperature or under warming.

More specifically, the object compound can be prepared by the processes described in Examples in the present application or similar processes.

The compounds obtained by the above-mentioned Process 1 can be isolated and purified by a conventional method, such as pulverization, recrystallization, column chromatography, high performance liquid chromatography (HPLC), reprecipitation and demineralized resin column chromatography.

In order to show the usefulness of the object compound (I) or a salt thereof in the present invention, a pharmacological test example of a representative compound in the present application is shown as follows.

TEST EXAMPLE

HCV Replicon Assay

The inhibitory activity against the replication of HCV replicon was evaluated by determining the amount of replicon RNA, purified from cell lysate with a conventional column method, using real-time RT-PCR based on Taq-Man chemistry. The assay was carried out with the modified method reported by Lohmann et al., *Science* 285: 100 (1999) and Takeuchi et al., *Gastroenterology* 116: 636-642 (1999). The details thereof are described in the following.

1) Addition of Agent to Cells $7.5 \times 10^3$ HCV replicon cells in 0.1 ml of D-MEM medium containing 5% fetal bovine serum and 300 µg/ml of G418 (Kishine et al., *B.B.R.C.* 293: 993-999 (2002)) were seeded in each well of a 96-well microtiter plate (Corning Inc.). After the plate was incubated at 37° C. for 16 hours in 5% $CO_2$, the medium was replaced with the above-mentioned medium in which the test compound was dissolved.

2) Extraction of RNA from Cells

After cultivation for two more days, total RNA was extracted from the cells according to the protocol of the RNA extraction column RNeasy96 (Qiagen Inc.).

3) Determination of the amount of replicon RNA According to the Real-Time RT-PCR Method The real-time RT-PCR was carried out by adding the appropriate primer set for amplifying the part of the HCV gene sequence and the complementary probe (all of these were produced by Takara Shuzo Co., Ltd.).

The RNA extracted at 2) was diluted with Nuclease-free water containing RNase inhibitor to 25 ng/µl, and dispensed to a 384-well PCR plate, 2 µl in each well. As the reaction solution for RT-PCR, TaqMan Ez RT-PCR Core Reagent (Applied Biosystems Inc.) was mixed according to the protocol and added, 8 µl in each well.

RT-PCR was carried out by using the ABI PRISM 7900HT sequence detection system (Applied Biosystems Inc.), and the gene copy number of the HCV replicon RNA in each cell was determined. Various concentrations of HCV RNA standard solutions, 10-fold serially diluted were used for the calibration curve creation. The reaction for negative control was carried out without RNA.

4) Measurement of Intrinsic Control RNA

As a further control for RNA recovery in each assay well, the copy number of cellular Glyceraldehyde-3-phosphate dehydrogenase (GAPDH) mRNA was quantified by real-time RT-PCR with specific primer set and probe (all of these were produced by Takara Shuzo Co., Ltd.) as described above (part3)

Estimation of Cellular Toxicity

The alamarBlue metabolic assay (Biosource International Inc.) was used to estimate the cytotoxicity in HCV replicon cells. After HCV replicon cells were cultured in the same conditions as those of the evaluation system of the replicon inhibitory activity, 5 µl of alamarBlue was added in each well, and the cells were further incubated at 37° C. for 2 hours in 5% $CO_2$. The fluorescence of each well was measured by spectrofluorometer (excitation 544 nm, emission 595 nm).

Test Method

The copy numbers of the replicon RNA in replicon cell treated at each concentrations of the compound, corrected by the intrinsic control GAPDH values at each point, were employed for the calculation of EC50 value of the compound, which gave the compound concentration indicating 50% RNA level to the control (no drug group, containing only DMSO). Similarly, the fluorescence values of the cells treated at each concentration of the compound were employed for the calculation of CC50 value, which gave the compound concentration indicating 50% level to the control (no drug group, containing only DMSO).

Test Result

Test Compound

The compound (2) of the Example 3.

TABLE 4

| Compound | HCV replicon inhibitory activity: EC50 (µM) |
| --- | --- |
| Compound(2) | <3 |

From the result of the above-mentioned test example, it is realized that the object compound (I) or a salt thereof of the present invention possesses an anti-hepatitis C virus activity.

The anti-HCV agent in the present invention, containing the compound (I) or a salt thereof as an active ingredient, can be used in the form of a pharmaceutical preparation, for example, in a solid, semisolid or liquid form, in admixture with an organic or inorganic carrier or excipient suitable for oral; sublingual; buccal; nasal; respiratory; parenteral (intracutaneous, intraorgan, subcutaneous, intradermal, intramuscular, intra-articular, central-venous, hepatic-venous, peripheral-venous, lymphatic, cardiovascular, arterial, ocular including injection around eye or intravenous drip around eye); intravenous drip into eyeball, augen structure or augen layer; aural including auditory canal, papillary chamber, external and internal auditory canals, drum membrane, tympanum, internal-auditory including spirals cochleae ganglion, labyrinth, etc.; intestinal; rectal; vaginal; ureteral; and vesical administration. With respect to intrauterine and perinatal adaptation diseases, parenteral administration is preferable since administration is carried out in maternal blood vessels, or in vacancies, such as maternal organs including uterus, uterine cervix and vagina; fetal embryo, fetus, neonate, and combination tissue; and amnion, umbilical cord, umbilical artery and vein; placenta, and the like. Use of these passages is changed depending on the condition of each patient.

The compound (I) or a salt thereof can be administered independently as a therapeutic agent or may be desired to be used as part of prescribed drugs. The "anti-HCV agent" in accordance with the present invention can be used in the form of a pharmaceutical preparation, for example, in a solid, semi-solid or liquid form, in admixture with at least one or some suitable organic or inorganic carriers or excipients, or other pharmacological therapeutic agents. The active ingredient can be compounded with, for example, usual pharmacologically acceptable and non-toxic carriers in a solid form, such as granules, tablets, pellets, troches, capsules or suppositories; creams; ointments: aerosols; powders for insufflation; in a liquid form, such as solutions, emulsions or suspensions for injection; oral ingestion; eye drops; and any other forms suitable for use. And, if necessary, there may be included in the above preparations auxiliary substances, such as stabilizing, thickening, wetting, hardening and coloring agents; perfumes or buffers; or any other additives used commonly.

The compound (I) or a pharmaceutically acceptable salt thereof is/are included in the pharmaceutical composition in an amount sufficient to produce the desired anti-hepatitis C effect upon the process or condition of diseases.

The combination use of IFN and/or ribavirin with the compound (I) or a salt thereof is effective against hepatitis C.

For applying the composition to humans, it is preferable to apply it by intravenous, intramuscular, pulmonary, oral administration, eye drop administration or insufflation. While the dosage of therapeutically effective amount of the compound (I) varies from and also depends upon the age and condition of each individual patient to be treated, in the case of intravenous administration, a daily dose of 0.001-400 mg of the compound (I) per kg weight of human being in the case of intramuscular administration, a daily dose of 0.1-20 mg of the compound (I) per kg weight of human being, in case of oral administration, a daily dose of 0.5-50 mg of the compound (I) per kg weight of human being is generally given for treating or preventing hepatitis C. However, these doses may be required to exceed the limit thereof to obtain therapeutic results.

The amount of the compound (I) or its pharmaceutically acceptable salt contained in the composition for a single unit dosage of the present invention is 0.1 to 400 mg, more preferably 1 to 200 mg, still more preferably 5 to 100 mg, specifically 5, 10, 15, 20, 25, 30, 35, 40, 45, 50, 55, 60, 65, 70, 75, 80, 85, 90, 95 and 100 mg.

An article of manufacture, comprising packaging material and the compound (I) identified in the above contained within said packaging material, wherein said the compound (I) is therapeutically effective for preventing or treating hepatitis C, and wherein said packaging material comprises a label or a written material which indicates that said compound (I) can or should be used for preventing or treating hepatitis C.

A commercial package comprising the pharmaceutical composition containing the compound (I) identified in the above and a written matter associated therewith, wherein the written matter states that the compound (I) can or should be used for preventing or treating hepatitis C.

It is to be noted that the compound (I) or a salt thereof may include one or more stereoisomer(s), such as optical isomer(s) and geometrical isomer(s), due to asymmetric carbon atom(s) and double bond(s), and that all such isomers and the mixture thereof are included within the scope of the present invention.

The compound (I) or a salt thereof may include solvated compound (e.g. hydrate, ethanolate, etc.).

The compound (I) or a salt thereof may include both the crystal form and non-crystal form.

The compound (I) or a salt thereof may include the prodrug form.

In addition the object compound (I) is useful as an intermediate for preparing a compound having an anti-hepatitis C virus activity.

The patent specifications and publications cited herein are incorporated in this specification by reference.

The following Examples are given for the purpose of illustrating the present invention. However, the present invention is not limited to these Examples.

Example 1

(1) Fermentation of *Lentzea* sp. No. 7887

A stock culture of *Lentzea* sp. No. 7887 is prepared and maintained on agar slant. A loopful of the slant culture was inoculated into a seed medium consisting of corn flour 1.0%, modified starch 6.0%, pharmamedia 1.2%, dried yeast 0.8%, $KH_2PO_4$ 0.3% and $MgSO_4.7H_2O$ 0.3% and $FeSO_4.7H_2O$ 0.02% (pH 6.5 adjusted with 6N NaOH). The inoculated vegetative medium (60 ml) was shaken on a rotary shaker (220 rpm, 5.1 cm throw) in a 225 ml Erlenmeyer flask at 30° C. for about 72 hours. And 3.2 ml of the seed culture was transferred to 160 ml of the sterile seed medium consisting of sucrose 0.5%, glucose 0.5%, oatmeal 0.5%, yeast extract 0.2%, peptone 0.5%, peanut powder 0.5%, "HUMAS" (Aiaisi kabushikikaisha, Osaka, Japan) as humic acid 0.01%, polyoxyethylene sorbitan monooleate 0.1% and $CaCO_3$ 0.2% (pH 7.0 adjusted with 6N NaOH) in the 500-ml Erlenmeyer flasks. The flasks were shaken on a rotary shaker (220 rpm, 5.1 cm throw) at 30° C. for about 72 hours, and 7.2 L (45 flasks) of the second culture was inoculated to sterile production medium (160 L and 200 L) consisting of corn flour 1.0%, modified starch 6.0%, pharmamedia 1.2%, dried yeast 0.8%, $KH_2PO_4$ 0.3% and $MgSO_4$ $7H_2O$ 0.3%, $FeSO_4.7H_2O$ 0.02%, Adekanol LG-109 0.05% and Silicone KM-70 0.05% (pH 6.5 adjusted with 6N NaOH). The inoculated production medium was allowed to ferment in 200 and 300 L jar fermentors at a temperature of 30° C. for about 72 hours. The fermentation medium was stirred with conventional agitators at 200 rpm and aerated at 160 L (200 L jar fermenter) or 200 L (300 L jar fermenter) per minute. The cultured broth was used as enzyme to produce the compound (I) from the compound (II).

(2) Reaction Condition

To a solution of the compound (IIb) disclosed below (180 g) in methanol (7.2 L) was added 360 L of the cultured broth obtained by above-mentioned fermentation. The mixture was carried out at 30° C. with stirring for 13 hours to give a reaction mixture (A). Increase of the compound (1), compound (2), compound (3), compound (4), compound (5), compound (6) and compound (7) were monitored by analytical HPLC indicated below.

Compound (IIb)

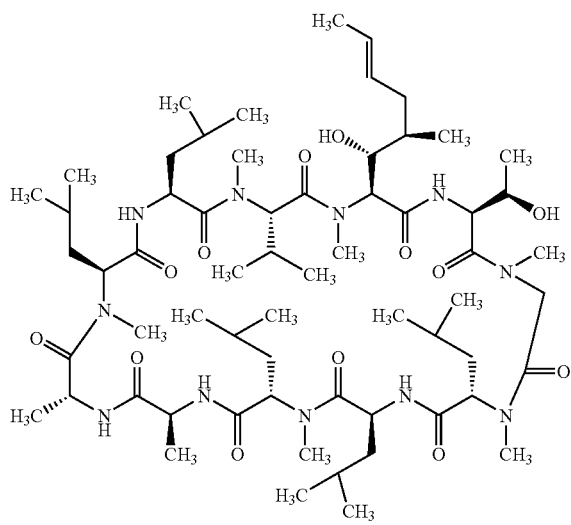

Analytical HPLC condition for compound (1), compound (2), compound (3) and compound (4)

| Column | Mightysil RP-8 GP 150-4.6 |  |
|---|---|---|
|  | (150 mm L. × 4.6 mm I.D., Kanto Chemical Co., Inc.) |  |
| Eluent | 60% aqueous acetonitrile containing 0.1% TFA |  |
| Flow rate | 1 ml/min. |  |
| Detection | UV at 210 nm |  |
| Retention time | Compound(1) | 7.6 min. |
|  | Compound(2) | 4.9 min. |
|  | Compound(3) | 6.4 min. |
|  | Compound(4) | 5.6 min. |

Analytical HPLC condition for compounds (5), compound (6) and compound (7)

| Column | Mightysil RP-18 GP 250-4.6 |  |
|---|---|---|
|  | (250 mm L. × 4.6 mm I.D., Kanto Chemical Co., Inc.) |  |
| Eluent | 50% aqueous acetonitrile containing 0.1% TFA |  |
| Flow rate | 1 ml/min. |  |
| Detection | UV at 210 nm |  |
| Retention time | Compound(5) | 9.4 min. |
|  | Compound(6) | 7.6 min. |
|  | Compound(7) | 8.3 min. |

Example 2

The reaction mixture (A) obtained in Example 1(2) (360 L) was extracted with an equal volume of acetone at room temperature. The mixture was filtered with an aid of diatomaceous earth. The filtrate was diluted with an equal volume of water and passed through a column (14 L) of DIAION HP-20 (Mitsubishi Chemical Co., Ltd.) packed with 25% aqueous acetone. The column was washed with 25% aqueous acetone (42 L) and then eluted with methanol (40 L). Active fraction (7-37 L) was diluted with equal volume of water and passed through a column (8 L) of Daisogel SP-120-ODS-B (15/30 mm, DAISO Co., Ltd., Japan) packed with 25% aqueous methanol. The column was washed with 50% aqueous acetonitrile (28 L) and eluted with 60% aqueous acetonitrile (24 L). Active fraction (12-24 L) was diluted with equal volume of water and passed through a column (2 L) of Daisogel SP-120-ODS-B (15/30 mm, DAISO Co., Ltd., Japan) packed with 30% aqueous acetonitrile. The column was eluted with 60% aqueous acetonitrile (7.5 L). Active fraction (5.1-7.1 L) was diluted with equal volume of water and passed through a column (2 L) of Daisogel SP-120-ODS-B (15/30 mm, DAISO Co., Ltd., Japan) packed with 30% aqueous acetonitrile. The column was eluted with 60% aqueous acetonitrile (14 L). Active fraction (5.8-8.1 L) was diluted with equal volume of water and passed through a column (2 L) of Daisogel SP-120-ODS-B (15/30 mm, DAISO Co., Ltd., Japan) packed with 30% aqueous acetonitrile. The column was eluted with 70% aqueous acetonitrile containing 0.1% TFA (6.4 L). Active fraction (2.8-3.6 L) was diluted with equal volume of water and passed through a column (2 L) of Daisogel SP-120-ODS-B (15/30 mm, DAISO Co., Ltd., Japan) packed with 35% aqueous acetonitrile containing 0.05% TFA. The column was washed with water (4 L) and eluted with ethylacetate (1.8 L). Active fraction (0-0.8 L) was concentrated to dryness under reduced pressure. The dried materials were dissolved in a small amount of chloroform, and were applied onto silica gel (Silica Gel 60 N, spherical, neutral, 40-100 μm, KANTO CHEMICAL Co., INC., 120 g). The column was washed with chloroform-methanol (98:2) and eluted with chloroform-methanol (97:3) and chloroform-methanol (95:5). Active fractions were collected and concentrated under reduced pressure to dryness. The dried materials were dissolved in a small amount of ethyl acetate and added to a large amount of n-hexane. And then, the compound (I) was precipitated, and filtered with glass filter. This precipitate was dried up under reduced pressure to give 3.7 g of the compound (I) as white powder.

The compound (I) has the following physico-chemical properties.

Appearance:
　White powder

Nature:
　Neutral substance

Melting Point:
　157-160° C. (dec.)

Specific Rotation:
　$[\alpha]^{23}_D$ −214° (c 1.0, $CH_2Cl_2$)

Molecular Formula:
　$C_{62}H_{111}N_{11}O_{14}$

Molecular Weight:
　ESI-MS (+) m/Z 1235 (M+H)

Solubility:
　Soluble: $CHCl_3$, MeOH, Ethyl acetate, Acetone, DMSO, Pyridine
　Slightly soluble: $H_2O$
　Insoluble: n-Hexane Color Reaction:
　Positive: iodine vapor reaction
　Negative:

Thin Layer Chromatography (TLC):
　Silica gel 60 F254 (Merck) $CHCl_3$:MeOH=10:1
　Rf 0.34

Infrared Absorption Spectrum: KBr
3420, 3330, 2960, 1630, 1520, 1410, 1100 cm$^{-1}$ The compound (1) exists in several stable conformations in a common organic solution. For one example, the $^{13}$C-NMR chemical shifts due to the major conformer of the compound (1) in pyridine-$d_5$ were listed as follows.

$^{13}$C-NMR (pyridine-$d_5$, 125 MHz)

δ: 175.1 (s), 174.4 (s), 174.4 (s), 173.4 (s), 173.0 (s), 172.9 (s), 171.0 (s), 171.0 (s), 170.4 (s), 169.5 (s), 169.0 (s), 133.9 (d), 128.7 (d), 74.9 (d), 69.6 (d), 63.1 (t), 61.4 (d), 59.3 (d), 57.3 (d), 55.7 (d), 55.6 (d), 54.6 (d), 49.0 (t), 48.6 (d), 48.1 (d), 47.4 (d), 46.6 (d), 41.2 (t), 41.1 (t), 39.1 (q), 38.5 (t), 38.2 (t), 37.3 (d), 36.8 (t), 36.7 (t), 34.1 (q), 31.0 (q), 30.8 (q), 29.9 (q), 28.8 (q), 27.6 (d), 25.9 (d), 25.6 (d), 25.3 (d), 24.9 (d), 24.8 (d), 24.1 (q), 23.6 (q), 23.3 (q), 23.2 (q), 23.2 (q), 23.2 (q), 22.8 (q), 21.5 (q), 21.2 (q), 20.9 (q), 19.7 (q), 19.3 (q), 18.3 (q), 17.4 (q), 16.2 (q), 15.4 (q)

From the analysis of the above physical and chemical, properties, and the result of the further investigation of identification of chemical structure, the chemical structure of the compound (1) has been identified and assigned as follows.

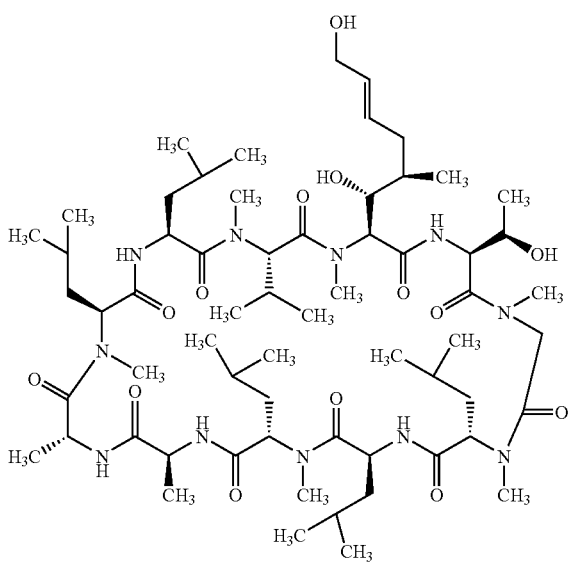

Example 3

The reaction mixture (A) obtained in Example 1(2) (360 L) was extracted with an equal volume of acetone at room temperature. The mixture was filtered with an aid of diatomaceous earth. The filtrate was diluted with an equal volume of water and passed through a column (14 L) of DIAION HP-20 (Mitsubishi Chemical Co., Ltd.) packed with 25% aqueous acetone. The column was washed with 25% aqueous acetone (42 L) and then eluted with methanol (40 L). Active fraction (7-37 L) was diluted with equal volume of water and passed through a column (8 L) of Daisogel SP-120-ODS-B (15/30 mm, DAISO Co., Ltd., Japan) packed with 25% aqueous methanol. The column was washed with 50% aqueous acetonitrile (28 L) and eluted with 60% aqueous acetonitrile (24 L). Active fraction (0-12 L) was diluted with equal volume of water and passed through a column (8 L) of Daisogel SP-120-ODS-B (15/30 mm, DAISO Co., Ltd., Japan) packed with 30% aqueous acetonitrile. The column was eluted with 60% aqueous acetonitrile (31 L). Active fraction (15.8-20.7 L) was diluted with equal volume of water and passed through a column (2 L) of Daisogel SP-120-ODS-B (15/30 mm, DAISO Co., Ltd., Japan) packed with 30% aqueous acetonitrile. The column was washed with water (5 L) and eluted with ethyl acetate (3.5 L). Active fraction (1-3 L) was concentrated to dryness under reduced pressure. The dried materials were dissolved in ethyl acetate (80 mL) and added dropwise to n-hexane (2.4 L). And then, the compound (2) was precipitated, and filtered with glass filter. This precipitate was dried up under reduced pressure to give 32.8 g of the compound (2) as white powder.

The compound (2) has the following physico-chemical properties.

Appearance:
White powder

Nature:
Neutral substance

Melting Point:
170-173° C. (dec.)

Specific Rotation:
$[α]^{23}_D$–222° (c 1.0, $CH_2Cl_2$)

Molecular Formula:
$C_{62}H_{111}N_{11}O_{14}$

Molecular Weight:
ESI-MS (+) m/Z 1235 (M+H)

Solubility:
Soluble: $CHCl_3$, MeOH, Ethyl acetate, Acetone, DMSO, Pyridine
Slightly soluble: $H_2O$
Insoluble: n-Hexane Color Reaction:
Positive: iodine vapor reaction
Negative:

Thin Layer Chromatography (TLC):
Silica gel 60 F254 (Merck) $CHCl_3$:MeOH=9:1
Rf 0.55

Infrared Absorption Spectrum: KBr
3420, 3330, 2960, 1640, 1530, 1410, 1100 cm$^{-1}$ The compound (2) exists in several stable conformations in a common organic solution. For one example, the $^{13}$C-NMR chemical shifts due to the major conformer of the compound (2) in pyridine-$d_5$ were listed as follows.

$^{13}$C-NMR (pyridine-$d_5$, 125 MHz)

δ: 175.3 (s), 174.5 (s), 174.4 (s), 173.4 (s), 173.0 (s), 172.9 (s), 171.0 (s), 170.9 (s), 170.5 (s), 169.5 (s), 169.0 (s), 129.8 (d), 127.1 (d), 75.2 (d), 69.6 (d), 67.9 (t), 61.5 (d), 59.3 (d), 57.3 (d), 55.7 (d), 55.3 (d), 54.6 (d), 49.0 (t), 48.6 (d), 48.1 (d), 47.4 (d), 46.6 (d), 41.2 (t), 41.0 (t), 39.1 (q), 38.5 (t), 38.2 (t), 37.6 (d), 37.3 (t), 34.1 (q), 33.5 (d), 31.5 (t), 31.0 (q), 30.8 (q), 29.9 (q), 28.8 (q), 27.7 (d), 25.9 (d), 25.6 (d), 24.9 (d), 24.8 (d), 24.1 (q), 23.3 (q), 23.2 (q), 23.2 (q), 23.2 (q), 22.8 (q), 21.2 (q), 20.9 (q), 19.6 (q), 19.3 (q), 18.3 (q), 18.1 (q), 17.4 (q), 16.2 (q), 16.1 (q), 15.4 (q)

The hydroxy group of the 2-threonine residue of the p-nitorophenylcarbonate derived from the compound (2) was converted into the t-butyldimethylsilyl ether. And it was hydrolyzed with 1N NaOH to give a compound (2a). The compound (2a) was crystallized from ethyl acetate and the absolute configuration was determined by X-ray analysis.

(2a)

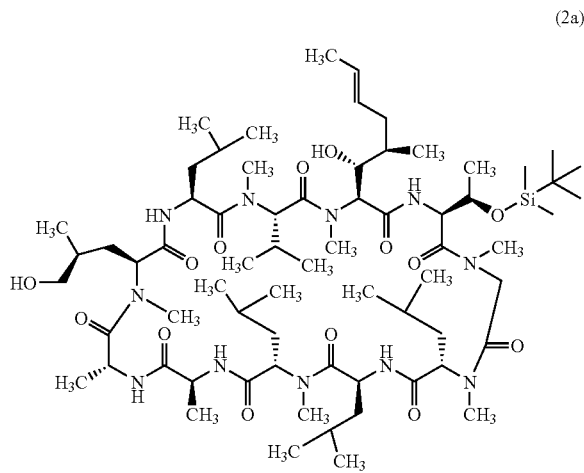

From the analysis of the above physical and chemical properties, the chemical structure of the compound (2) including stereochemistry has been identified and assigned as follows.

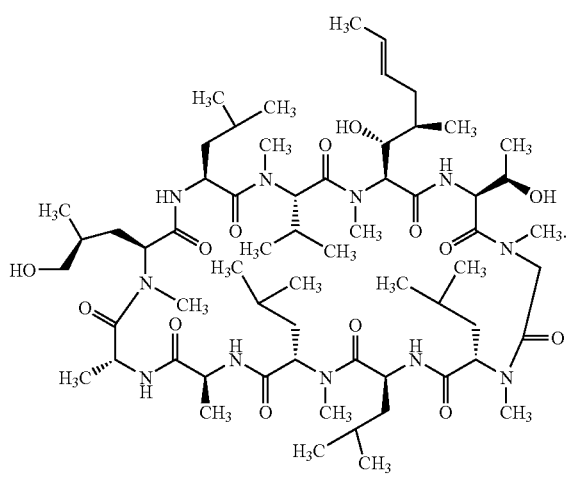

Example 4

The reaction mixture (A) obtained in Example 1(2) (360 L) was extracted with an equal volume of acetone at room temperature. The mixture was filtered with an aid of diatomaceous earth. The filtrate was diluted with an equal volume of water and passed through a column (14 L) of DIAION HP-20 (Mitsubishi Chemical Co. Ltd.) packed with 25% aqueous acetone. The column was washed with 25% aqueous acetone (42 L) and then eluted with methanol (40 L). Active fraction (7-37 L) was diluted with equal volume of water and passed through a column (8 L) of Daisogel SP-120-ODS-B (15/30 mm, DAISO Co., Ltd., Japan) packed with 25% aqueous methanol. The column was washed with 50% aqueous acetonitrile (28 L) and eluted with 60% aqueous acetonitrile (24 L). Active fraction (0-12 L) was diluted with equal volume of water and passed through a column (8 L) of Daisogel SP-120-ODS-B (15/30 mm, DAISO Co., Ltd., Japan) packed with 30% aqueous acetonitrile. The column was eluted with 60% aqueous acetonitrile (31 L). Active fraction (20.7-24.7 L) was diluted with equal volume of water and passed through a column (2 L) of Daisogel SP-120-ODS-B (15/30 mm, DAISO Co., Ltd., Japan) packed with 30% aqueous acetonitrile. The column was eluted with 60% aqueous acetonitrile (9 L). Active fraction (6.7-8.7 L) was diluted with equal volume of water and passed through a column (1 L) of Daisogel SP-120-ODS-B (15/30 mm, DAISO Co., Ltd., Japan) packed with 30% aqueous acetonitrile. The column was eluted with 60% aqueous acetonitrile (4 L). Active fraction (3.0-3.7 L) was concentrated in vacuo to give 322 mg of the compound (3) as pale yellow powder.

The compound (3) has the following physico-chemical properties.

Appearance:
  Pale yellow powder

Nature:
  Neutral substance

Melting Point:
  162-165° C. (dec.)

Specific Rotation:
  $[\alpha]^{23}_D$ –200° (c 1.0, $CH_2Cl_2$)

Molecular Formula:
  $C_{62}H_{111}N_{11}O_{14}$

Molecular Weight:
  ESI-MS (+) m/Z 1235 (M+H)

Solubility:
  Soluble: $CHCl_3$, MeOH, Ethyl acetate, Acetone, DMSO, Pyridine
  Slightly soluble: $H_2O$
  Insoluble: n-Hexane Color Reaction:
  Positive: iodine vapor reaction
  Negative:

Thin Layer Chromatography (TLC):
  Silica gel 60 F254 (Merck) $CDCl_3$:MeOH=9:1
  Rf 0.50

Infrared Absorption Spectrum: KBr
  3420, 3330, 2960, 1640, 1530, 1410, 1280, 1100 $cm^{-1}$ The compound (3) exists in several stable conformations in a common organic solution. For one example, the $^{13}$C-NMR chemical shifts due to the major conformer of the compound (3) in pyridine-$d_5$ were listed as follows.

$^{13}$C-NMR (pyridine-$d_5$, 125 MHz)
  δ: 174.7 (s), 174.5 (s), 174.3 (s), 173.4 (s), 173.0 (s), 172.9 (s), 171.1 (s), 171.0 (s), 170.9 (s), 169.5 (s), 169.0 (s), 129.8 (d), 127.1 (d), 75.2 (d), 69.6 (d), 69.1 (s), 61.5 (d), 59.3 (d), 57.3 (d), 55.7 (d), 55.0 (d), 54.6 (d), 49.0 (t), 48.9 (d), 48.1 (d), 47.4 (d), 46.6 (d), 41.3 (t), 41.3 (t), 41.0 (t), 39.1 (q), 38.6 (t), 38.2 (t), 37.6 (d), 37.3 (t), 34.1 (q), 31.8 (q), 31.0 (q), 30.4 (q), 29.9 (q), 29.8 (q), 28.8 (q), 27.6 (d), 25.9 (d), 25.6 (d), 24.9 (d), 24.8 (d), 24.1 (q), 23.3 (q), 23.3 (q), 23.2 (q), 23.2 (q), 22.8 (q), 21.2 (q), 20.9 (q), 19.6 (q), 19.3 (q), 18.3 (q), 18.1 (q), 17.4 (q), 16.1 (q), 15.0 (q)

From the analysis of the above physical and chemical properties, and the result of the further investigation of identification of chemical structure, the chemical structure of the compound (3) has been identified and assigned as follows.

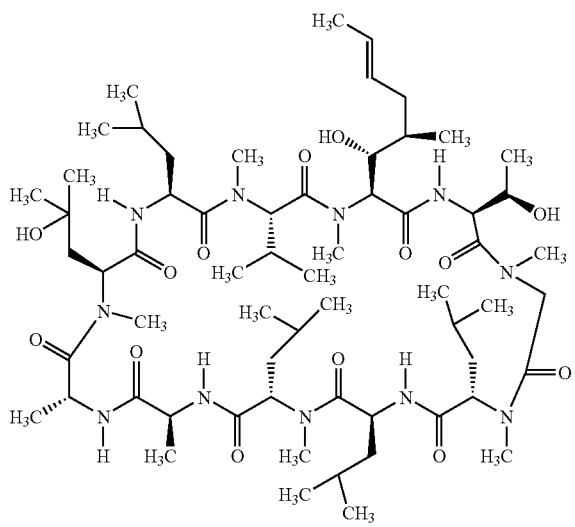

Example 5

The reaction mixture (A) obtained in Example 1(2) (360 L) was extracted with an equal volume of acetone at room temperature. The mixture was filtered with an aid of diatomaceous earth. The filtrate was diluted with an equal volume of water and passed through a column (14 L) of DIAION HP-20 (Mitsubishi Chemical Co., Ltd.) packed with 25% aqueous acetone. The column was washed with 25% aqueous acetone (42 L) and then eluted with methanol (40 L). Active fraction (7-37 L) was diluted with equal volume of water and passed through a column (8 L) of Daisogel SP-120-ODS-B (15/30 mm, DAISO Co., Ltd., Japan) packed with 25% aqueous methanol. The column was washed with 50% aqueous acetonitrile (28 L) and eluted with 60% aqueous acetonitrile (24 L). Active fraction (0-12 L) was diluted with equal volume of water and passed through a column (8 L) of Daisogel SP-120-ODS-B (15/30 mm, DAISO Co., Ltd., Japan) packed with 30% aqueous acetonitrile. The column was eluted with 60% aqueous acetonitrile (31 L). Active fraction (20.7-24.7 L) was diluted with equal volume of water and passed through a column (2 L) of Daisogel SP-120-ODS-B (15/30 mm, DAISO Co., Ltd., Japan) packed with 30% aqueous acetonitrile. The column was eluted with 60% aqueous acetonitrile (9 L). Active fraction (5.1-6.1 L) was diluted with equal volume of water and passed through a column (1 L) of Daisogel SP-120-ODS-B (15/30 mm, DAISO Co., Ltd., Japan) packed with 30% aqueous acetonitrile. The column was eluted with 60% aqueous acetonitrile (4.7 L). Active fraction (2.7-2.9 L) was concentrated in vacuo to give 740 mg of the compound (4) as pale yellow powder.

The compound (4) has the following physico-chemical properties.

Appearance:
  Pale yellow powder

Nature:
  Neutral substance

Melting Point:
  162-165° C. (dec.)

Specific Rotation:
  $[\alpha]^{23}_D$ −215° (c 1.0, $CH_2Cl_2$)

Molecular Formula:
  $C_{62}H_{111}N_{11}O_{14}$

Molecular Weight:
  ESI-MS (+) m/Z 1235 (M+H)

Solubility:
  Soluble: $CHCl_3$, MeOH, Ethyl acetate, Acetone, DMSO, Pyridine
  Slightly soluble: $H_2O$
  Insoluble: n-Hexane Color Reaction:
  Positive: iodine vapor reaction
  Negative:

Thin Layer Chromatography (TLC):
  Silica gel 60 F254 (Merck) $CDCl_3$:MeOH=9:1
  Rf 0.5

Infrared Absorption Spectrum: KBr
  3420, 3330, 2960, 1880, 1640, 1520, 1410, 1280, 1100 $cm^{-1}$ The compound (4) exists in several stable conformations in a common organic solution. For one example, the $^{13}$C-NMR chemical shifts due to the major conformer of the compound (4) in pyridine-$d_5$ were listed as follows.

$^{13}$C-NMR (pyridine-$d_5$, 125 MHz)
  δ: 175.1 (s), 174.4 (s), 174.4 (s), 173.4 (s), 173.0 (s), 172.9 (s), 171.0 (s), 170.9 (s), 170.4 (s), 169.5 (s), 169.0 (s), 129.8 (d), 127.1 (d), 75.2 (d), 69.6 (d), 66.1 (t), 61.5 (d), 59.3 (d), 57.3 (d), 55.7 (d), 55.7 (d), 54.6 (d), 49.0 (t), 48.6 (d), 48.1 (d), 47.4 (d), 46.6 (d), 41.2 (t), 41.2 (t), 39.1 (q), 38.5 (t), 38.2 (t), 37.6 (d), 37.3 (t), 34.1 (q), 34.0 (d), 31.6 (t), 31.1 (q), 31.0 (q), 29.9 (q), 28.8 (q), 27.7 (d), 25.9 (d), 25.6 (d), 24.9 (d), 24.8 (d), 24.1 (q), 23.2 (q), 23.2 (q), 23.2 (q), 23.2 (q), 22.8 (q), 21.3 (q), 20.9 (q), 19.7 (q), 19.3 (q), 18.4 (q), 18.1 (q), 18.1 (q), 17.4 (q), 16.1 (q), 15.3 (q)

From the analysis of the above physical and chemical properties, and the result of the further investigation of identification of chemical structure, the chemical structure of the compound (4) has been identified and assigned as follows.

And the stereochemistry of N-methyl-hydroxyleucine in the compound (4) was determined by $^{13}$C-NMR data comparison with that of the compound (2).

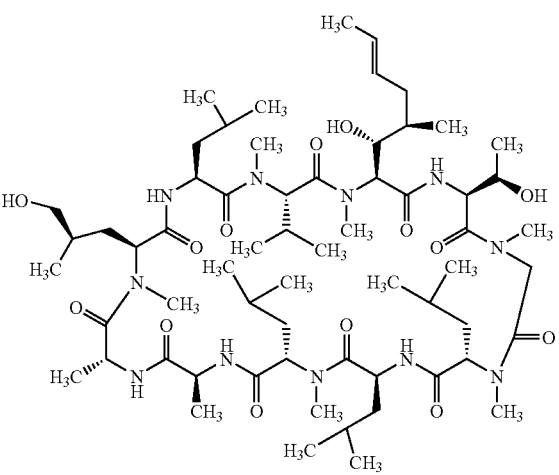

Example 6

The reaction mixture (A) obtained in Example 1(2) (360 L) was extracted with an equal volume of acetone at room temperature. The mixture was filtered with an aid of diatomaceous earth. The filtrate was diluted with an equal volume of water and passed through a column (14 L) of DIAION HP-20 (Mitsubishi Chemical Co., Ltd.) packed with 25% aqueous acetone. The column was washed with 25% aqueous acetone (42 L) and then eluted with methanol (40 L). Active fraction (7-37 L) was diluted with equal volume of water and passed through a column (8 L) of Daisogel SP-120-ODS-B (15/30 mm, DAISO Co., Ltd., Japan) packed with 25% aqueous methanol. The column was eluted with 50% aqueous acetonitrile (28 L). Active fraction (15-28 L) was diluted with equal volume of water and passed through a column (8 L) of Daisogel SP-120-ODS-B (15/30 mm, DAISO Co., Ltd., Japan) packed with 25% aqueous acetonitrile. The column was eluted with 50% aqueous acetonitrile Active fraction (18.8-20.8 L) was concentrated under reduced pressure to remove acetone and extracted with 1 L of ethyl acetate. The solvent extract (upper layer) was concentrated under reduced pressure to an oily residue. The dried materials were dissolved in a small amount of chloroform, and were applied onto silica gel (Silica Gel 60N, spherical, neutral, 40-100 μm, KANTO CHEMICAL Co., INC., 50 g). The column was washed with chloroform-methanol (97:3) and eluted with chloroform-methanol (96:4) and chloroform-methanol (95:5). Active fractions were collected and concentrated under reduced pressure to dryness. The dried materials were dissolved in a small amount of methanol and subjected to preparative HPLC, (Mightysil RP-18 GP 250-20 (5 mm), KANTO CHEMICAL Co., INC.). The column was developed with 50% aqueous acetonitrile containing 0.1% TFA at a flow rate of 10 ml/minute. The active fraction was diluted with a equal volume of water and passed through a column (19 ml) of Daisogel SP-120-ODS-B (15/30 mm, DAISO Co., Ltd., Japan) packed with 25% aqueous methanol containing 0.05% TFA. The column was washed with water (50 ml) and eluted with ethyl acetate (50 ml). The elute was concentrated to dryness under reduced pressure. The dried materials were dissolved in a small amount of ethyl acetate and added to a large amount of n-hexane. And then, the compound (5) was precipitated, and filtered with glass filter. This precipitate was dried up under reduced pressure to give 205 mg of the compound (5) as white powder.

The compound (5) has the following physico-chemical properties.

Appearance:
  white powder

Nature:
  Neutral substance

Melting Point:
  163-167° C. (dec.)

Specific Rotation:
  $[\alpha]^{23}{}_D$ –1990 (c 1.0, $CH_2Cl_2$)

Molecular Formula:
  $C_{62}H_{111}N_{11}O_{15}$

Molecular Weight:
  ESI-MS (+) m/Z 1251 (M+H)

Solubility:
  Soluble: $CHCl_3$, MeOH, Ethyl acetate, Acetone, DMSO, Pyridine
  Slightly soluble: $H_2O$
  Insoluble: n-Hexane Color Reaction:
  Positive: iodine vapor reaction
  Negative:

Thin Layer Chromatography (TLC):
  Silica gel 60 F254 (Merck) $CHCl_3$:MeOH=10:1
  Rf 0.42

Infrared Absorption Spectrum: KBr
  3420, 3330, 2960, 1630, 1530, 1410, 1100 $cm^{-1}$ The compound (5) exists in several stable conformations in a common organic solution. For one example, the $^{13}$C-NMR chemical shifts due to the major conformer of the compound (5) in pyridine-$d_5$ were listed as follows.

$^{13}$C-NMR (pyridine-$d_5$, 125 MHz)
  δ: 174.7 (s), 174.5 (s), 174.3 (s), 173.4 (s), 173.0 (s), 172.9 (s), 171.1 (s), 171.0 (s), 170.9 (s), 169.5 (s), 169.0 (s), 133.9 (d), 128.7 (d), 74.9 (d), 69.6 (d), 69.0 (s), 63.1 (t), 61.4 (d), 59.3 (d), 57.3 (d), 55.7, (d), 55.0 (d), 54.6 (d); 49.0 (t), 48.9 (d), 48.1 (d), 47.4 (d), 46.6 (d), 41.3 (t), 41.3 (t), 41.1 (t), 39.1 (q), 38.6 (t), 38.2 (t), 37.3 (d), 36.8 (t), 34.1 (q), 31.7 (q), 31.0 (q), 30.4 (q), 29.9 (q), 29.8 (q), 28.8 (q), 27.6 (d), 25.9 (d), 25.6 (d), 24.9 (d), 24.8 (d), 24.1 (q), 23.3 (q), 23.3 (q), 23.2 (q), 23.2 (q), 22.8 (q), 21.2 (q), 20.9 (q), 19.7 (q), 19.3 (q), 18.3 (q), 17.5 (q), 16.2 (q), 15.0 (q)

From the analysis of the above physical and chemical properties, and the result of the further investigation of identification of chemical structure, the chemical structure of the compound (5) has been identified and assigned as follows.

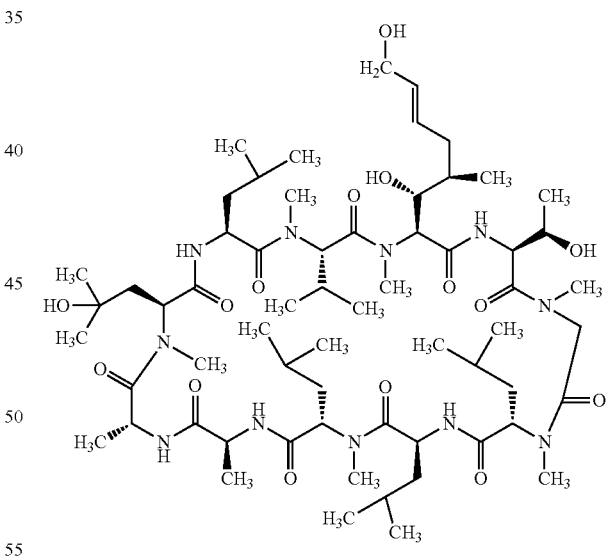

Example 7

The reaction mixture (A) obtained in Example 1(2) (360 L) was extracted with an equal volume of acetone at room temperature. The mixture was filtered with an aid of diatomaceous earth. A part of filtrate was diluted with an equal volume of water and passed through a column (2 L) of Daisogel SP-120-ODS-B (15/30 mm, DAISO Co., Ltd., Japan) packed with 25% acetone. The column was eluted with 50% aqueous acetonitrile (10 L). Active fraction (2.6-4.6 L) was diluted with equal volume of water and passed through a column (2 L) of Daisogel SP-120-ODS-B (15/30 mm, DAISO Co., Ltd., Japan) packed with 25% aqueous acetonitrile. The column was eluted with 45% aqueous acetonitrile containing 0.1% TFA (13 L). Active fraction (8.6-9.6 L) was diluted with equal volume of water and passed through a column (2 L) of Daisogel SP-120-ODS-B (15/30 mm, DAISO CO., Ltd., Japan) packed with 22.5% aqueous acetonitrile containing 0.05% TFA. The column was washed with water (5 L) and eluted with ethyl acetate (2 L). Active fraction (0-0.5 L) was concentrated to dryness under reduced pressure. The dried materials were dissolved in a small amount of ethyl acetate and added to a large amount of n-hexane. And then, the compound (6) was precipitated. This precipitate was dried up under reduced pressure to give 1.3 g of the compound (6) as pale yellow powder.

The compound (6) has the following physico-chemical properties.

Appearance:
  Pale yellow powder

Nature:
  Neutral substance

Melting Point:
  163-167° C. (dec.)

Specific Rotation:
  $[\alpha]^{23}_D -207 < (c\ 1.0, CH_2Cl_2)$

Molecular Formula:
  $C_{62}H_{111}N_{11}O_{15}$

Molecular Weight:
  ESI-MS (+) m/Z 1251 (M+H)

Solubility:
  Soluble: $CHCl_3$, MeOH, Ethyl acetate, Acetone, DMSO, Pyridine
  Slightly soluble: $H_2O$
  Insoluble: n-Hexane Color Reaction:
  Positive: iodine vapor reaction
  Negative:

Thin Layer Chromatography (TLC):
  Silica gel 60 F254 (Merck) $CHCl_3$:MeOH=9:1
  Rf 0.29

Infrared Absorption Spectrum: KBr
  3420, 3330, 2960, 1630, 1530, 1410, 1100 $cm^{-1}$ The compound (6) exists in several stable conformations in a common organic solution. For one example, the $^{13}C$-NMR chemical shifts due to the major conformer of the compound (6) in pyridine-$d_5$ were listed as follows.

$^{13}C$-NMR (pyridine-$d_5$, 125 MHz)
  δ: 175.2 (s), 174.5 (s), 174.4 (s), 173.4 (s), 173.0 (s), 172.9 (s), 171.0 (s), 170.9 (s), 170.5 (s), 169.5 (s), 169.0 (s), 133.9 (d), 128.7 (d), 75.0 (d), 69.6 (d), 67.9 (t), 63.1 (t), 61.4 (d), 59.3 (d), 57.3 (d), 55.7 (d), 55.3 (d), 54.6 (d), 49.0 (t), 48.6 (d), 48.1 (d), 47.4 (d), 46.6 (d), 41.2 (t), 41.1 (t), 39.1 (q), 38.5 (t), 38.2 (t), 37.3 (d), 36.8 (t), 34.1 (q), 33.5 (d), 31.5 (t), 31.0 (q), 30.8 (q), 29.9 (q), 28.8 (q), 27.6 (d), 25.9 (d), 25.6 (d), 24.9 (d), 24.8 (d), 24.1 (q), 23.3 (q), 23.2 (q), 23.2 (q), 23.2 (q), 22.8 (q), 21.2 (q), 20.9 (q), 19.7 (q), 19.3 (q), 18.3 (q), 17.4 (q), 16.2 (q), 16.2 (q), 15.4 (q)

From the analysis of the above physical and chemical properties, and the result of the further investigation of identification of chemical structure, the chemical structure of the compound (6) has been identified and assigned as follows.

And the stereochemistry of N-methyl-hydroxyleucine in the compound (6) was defined by $^{13}C$-NMR data comparison with that of the compound (2).

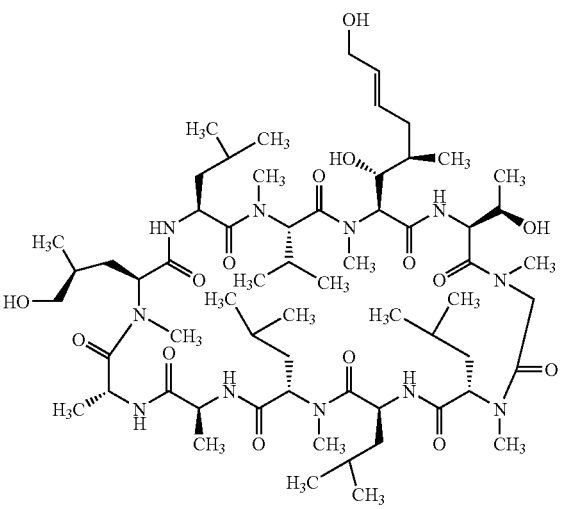

Example 8

The reaction mixture (A) obtained in Example 1(2) (360 L) was extracted with an equal volume of acetone at room temperature. The mixture was filtered with an aid of diatomaceous earth. The filtrate was diluted with an equal volume of water and passed through a column (14 L) of DIAION HP-20 (Mitsubishi Chemical Co., Ltd.) packed with 25% aqueous acetone. The column was washed with 25% aqueous acetone (42 L) and then eluted with methanol (40 L). Active fraction (7-37 L) was diluted with equal volume of water and passed through a column (8 L) of Daisogel SP-120-ODS-B (15/30 mm, DAISO Co., Ltd., Japan) packed with 25% aqueous methanol. The column was eluted with 50% aqueous acetonitrile (28 L). Active fraction (15-28 L) was diluted with equal volume of water and passed through a column (8 L) of Daisogel SP-120-ODS-B (15/30 mm, DAISO Co., Ltd., Japan) packed with 25% aqueous acetonitrile. The column was eluted with 50% aqueous acetonitrile. Active fraction (17.8-18.8 μL) was concentrated under reduced pressure to remove acetone and extracted with 500 ml of ethyl acetate. The solvent extract (upper layer) was concentrated under reduced pressure to an oily residue. The dried materials were dissolved in a small amount of chloroform, and were applied onto silica gel (Silica Gel 60 N, spherical, neutral, 40-100 μm, KANTO CHEMICAL Co., INC., 50 g). The column was washed with chloroform-methanol (97:3) and eluted with chloroform-methanol (96:4) and chloroform-methanol (95:5). Active fractions were collected and concentrated under reduced pressure to dryness. The dried materials were dissolved in a small amount of methanol and subjected to preparative HPLC, (Mightysil RP-18 GP 250-20 (5 mm), KANTO CHEMICAL Co., INC.). The column was developed with 50% aqueous acetonitrile containing 0.1% TFA at a flow rate of 10 ml/minute. The active fraction was diluted with an equal volume of water and passed through a column (19 ml) of Daisogel SP-120-ODS-B (15/30 mm, DAISO Co., Ltd., Japan) packed with 25% aqueous methanol containing 0.05% TFA. The column was washed with water (50 ml) and eluted with ethyl acetate (50 ml). The eluate was concentrated to dryness under reduced pressure. The dried materials were dissolved in a small amount of ethyl acetate and added to a large amount of n-hexane. And then, the compound (7) was precipitated, and filtered with glass filter. This precipitate was dried up under reduced pressure to give 227 mg of the compound (7) as white powder.

The compound (7) has the following physico-chemical properties.

Appearance:
White powder

Nature:
Neutral substance

Melting Point:
163-167° C. (dec.)

Specific Rotation:
$[\alpha]^{23}_D$ −1990 (c 1.0, $CH_2Cl_2$)

Molecular Formula:
$C_{62}H_{111}N_{11}O_{15}$

Molecular Weight:
ESI-MS (+) m/Z 1251 (M+H)

Solubility:
Soluble: $CHCl_3$, MeOH, Ethyl, acetate, Acetone, DMSO, Pyridine
Slightly soluble: $H_2O$
Insoluble: n-Hexane Color Reaction:
Positive: iodine vapor reaction
Negative:

Thin Layer Chromatography (TLC):
Silica gel 60 F254 (Merck) $CHCl_3$:MeOH 10:1
Rf 0.41

Infrared Absorption Spectrum: KBr
3420, 3330, 2960, 1630, 1520, 1410, 1100 $cm^{-1}$ The compound (7) exists in several stable conformations in a common organic solution. For one example, the $^{13}C$-NMR chemical shifts due to the major conformer of the compound (7) in pyridine-$d_5$ were listed as follows.

$^{13}C$-NMR (pyridine-$d_5$, 125 MHz)
δ: 175.1 (s), 174.4 (s), 174.4 (s), 173.4 (s), 172.9 (s), 172.9 (s), 171.0 (s), 170.9 (s), 170.4 (s), 169.5 (s), 169.0 (s), 133.9 (d), 128.7 (d), 75.0 (d), 69.6 (d), 66.1 (t), 63.1 (t), 61.4 (d), 59.3 (d), 57.3 (d), 55.7 (d), 55.7 (d), 54.6 (d), 49.0 (t), 48.6 (d), 48.1 (d), 47.4 (d), 46.6 (d), 41.3 (t), 41.2 (t), 39.1 (q), 38.5 (t), 38.2 (t), 37.3 (d), 36.8 (t), 34.1 (q), 34.0 (d), 31.6 (t), 31.1 (q), 31.0 (q), 29.9 (q), 28.8 (q), 27.7 (d), 25.9 (d), 25.6 (d), 24.9 (d), 24.8 (d), 24.1 (q), 23.2 (q), 23.2 (q), 23.2 (q), 23.2 (q), 22.8 (q), 21.2 (q), 20.9 (q), 19.7 (q), 19.3 (q), 18.4 (q), 18.1 (q), 17.4 (q), 16.2 (q), 15.3 (q)

From the analysis of the above physical and chemical properties, and the result of the further investigation of identification of chemical structure, the chemical structure of the compound (7) has been identified and assigned as follows.

And the stereochemistry of N-methyl-hydroxyleucine in the compound (7) was determined by $^{13}C$-NMR data comparison with that of the compound (4).

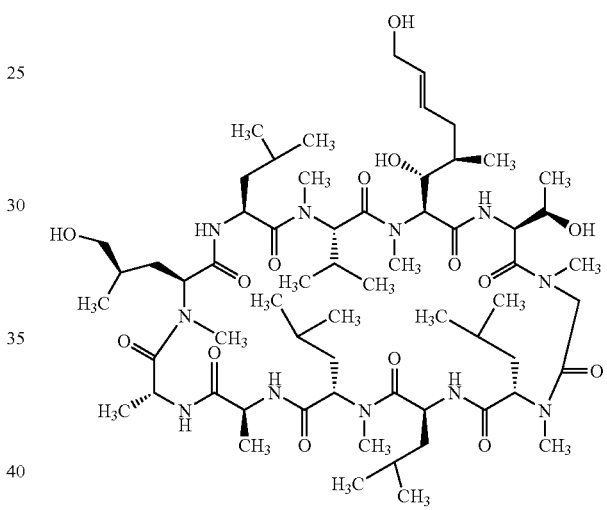

The invention claimed is:

1. A cyclic peptide compound of the following general formula (I):

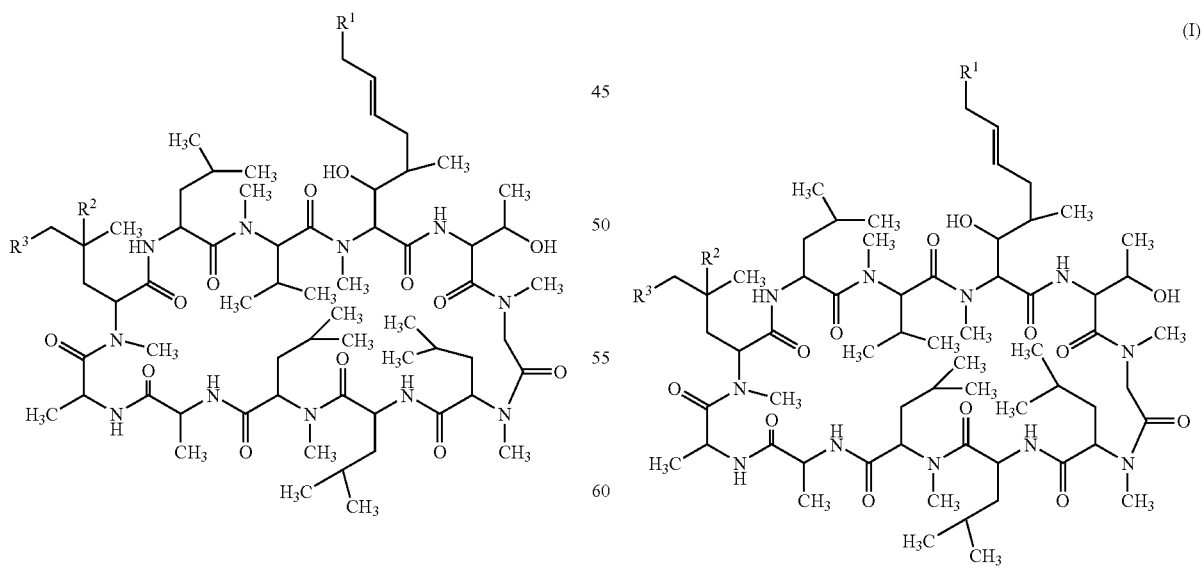

wherein
$R^1$ is hydrogen or hydroxy,
$R^2$ is hydrogen or hydroxy, and
$R^3$ is hydrogen or hydroxy, Providing that when $R^1$ is hydrogen,
then at least one of $R^2$ and $R^3$ is hydroxy, or a salt thereof.

2. A process of producing a cyclic peptide compound (I) of the following formula (I):

[wherein $R^1$, $R^2$ and $R^3$ are defined above], or a salt thereof, which comprises contacting a cyclic peptide compound (II) of the following formula (II):

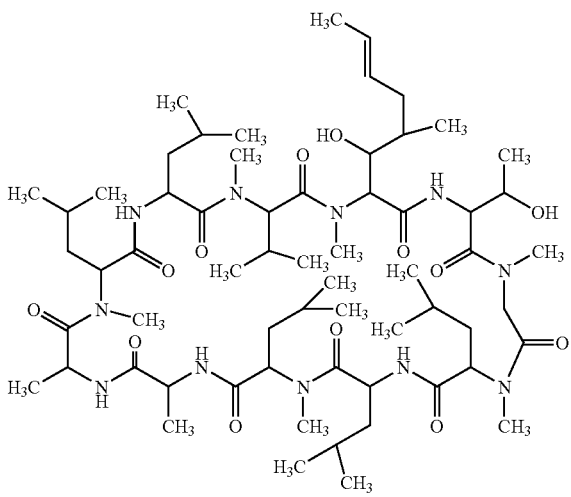

(II)

or a salt thereof, with an enzyme obtained by culturing an enzyme-producing strain of microorganism belonging to the genus *Lentzea*.

3. The process of claim 2, wherein the strain of microorganism is *Lentzea* sp. No. 7887.

4. A pharmaceutical composition which comprises, as an active ingredient, a compound of claim 1 or a pharmaceutically acceptable salt thereof in admixture with pharmaceutically acceptable carriers or excipients.

5. A compound of claim 1 or a pharmaceutically acceptable salt thereof for use as a medicament.

6. A method for making a medicament, which comprises using a compound of claim 1 or a pharmaceutically acceptable salt thereof.

7. A method for the therapeutic treatment of hepatitis C, which comprises administering a compound of claim 1 or a pharmaceutically acceptable salt thereof to a human being or an animal.

8. A commercial package comprising the pharmaceutical composition of claim 4 and a written matter associated therewith, wherein the written matter states that the pharmaceutical composition can or should be used for treating hepatitis C.

9. An article of manufacture, comprising packaging material and the compound (I) identified in claim 1 contained within said packaging material, wherein said compound (I) is therapeutically effective for treating hepatitis C, and wherein said packaging material comprises a label or a written material which indicates that said compound (I) can or should be used for treating hepatitis C.

* * * * *

SEQUENCE LISTING

```
<160> NUMBER OF SEQ ID NOS: 1

<210> SEQ ID NO 1
<211> LENGTH: 1465
<212> TYPE: DNA
<213> ORGANISM: Lentzea sp. No. 7887

<400> SEQUENCE: 1
cgaacgctgg cggcgtgctt aacacatgca agtcgagcgg taaggccctt cggggtacac      60
gagcggcgaa cgggtgagta acacgtgggt aacctgccct gtactctggg ataagccttg     120
gaaacgaggt ctaataccgg atacgaccat tgatcgcatg atcggtggtg gaaagttccg     180
gcggtatggg atgacccgc ggcctatcag cttgttggtg gggtaatggc ctaccaaggc      240
gacgacgggt agccggcctg agagggtgac cggccacact gggactgaga cacggcccag     300
actcctacgg gaggcagcag tggggaatat tgcacaatgg gcgaaagcct gatgcagcga     360
```

-continued

```
cgccgcgtga gggatgacgg ccttcgggtt gtaaacctct ttcagcaggg acgaagcgca    420
agtgacggta cctgcagaag aagcaccggc taactacgtg ccagcagccg cggtaatacg    480
tagggtgcga gcgttgtccg gaattattgg gcgtaaagag ctcgtaggcg gtttgtcgcg    540
tcggccgtga aaacttgggg cttaactcca agcttgcggt cgatacgggc agacttgagt    600
tcggcagggg agactggaat tcctggtgta gcggtgaaat gcgcagatat caggaggaac    660
accggtggcg aaggcgggtc tctgggccga tactgacgct gaggagcgaa agcgtgggga    720
gcgaacagga ttagataccc tggtagtcca cgccgtaaac ggtgggtgct aggtgtgggg    780
ggcttccacg ccctctgtgc cgcagctaac gcattaagca ccccgcctgg ggagtacggc    840
cgcaaggcta aaactcaaag gaattgacgg gggcccgcac aagcggcgga gcatgtggat    900
taattcgatg caacgcgaag aaccttacct gggcttgaca tggactagaa agctctagag    960
atagagcctc ccttgtggct ggttcacagg tggtgcatgg ctgtcgtcag ctcgtgtcgt   1020
gagatgttgg gttaagtccc gcaacgagcg caaccctcgt tccatgttgc cagcacgtaa   1080
tggtggggac tcatgggaga ctgccggggt caactcggag gaaggtgggg atgacgtcaa   1140
gtcatcatgc cccttatgtc cagggcttca cacatgctac aatggccggt acaaagggct   1200
gctaagccgt gaggtggagc gaatcccata aagccggtct cagttcggat cggggtctgc   1260
aactcgaccc cgtgaagtcg gagtcgctag taatcgcaga tcagcaacgc tgcggtgaat   1320
acgttcccgg gccttgtaca caccgcccgt cacgtcacga aagtcggtaa cacccgaagc   1380
ccgtggctca acccgcaagg gggagagcgg tcgaaggtgg gactggcgat tgggacgaag   1440
tcgtaacaag gtagccgtac cggaa                                         1465
```